(12) United States Patent
Ruff

(10) Patent No.: US 11,020,437 B2
(45) Date of Patent: *Jun. 1, 2021

(54) METHODS FOR TREATING NUCLEAR FACTOR KAPPA-LIGHT-CHAIN-ENHANCER OF ACTIVATED B CELL (NF-KB) DYSREGULATION IN A HOST IN NEED THEREOF USING EGGSHELL MEMBRANE COMPOSITIONS

(71) Applicant: ESM Technologies, LLC, Carthage, MO (US)

(72) Inventor: Kevin J. Ruff, Carthage, MO (US)

(73) Assignee: ESM TECHNOLOGIES, LLC, Carthage, MO (US)

(*) Notice: Subject to any disclaimer, the term of this patent is extended or adjusted under 35 U.S.C. 154(b) by 14 days.

This patent is subject to a terminal disclaimer.

(21) Appl. No.: 16/433,683

(22) Filed: Jun. 6, 2019

(65) Prior Publication Data
US 2019/0365824 A1 Dec. 5, 2019

Related U.S. Application Data

(62) Division of application No. 15/528,335, filed as application No. PCT/US2015/054742 on Oct. 8, 2015, now Pat. No. 10,328,104.

(51) Int. Cl.
| | | |
|---|---|---|
| A61K 35/57 | (2015.01) |
| A61K 38/43 | (2006.01) |
| A61K 35/741 | (2015.01) |
| A61P 29/00 | (2006.01) |
| A61P 37/06 | (2006.01) |
| A61P 35/00 | (2006.01) |
| A61K 45/06 | (2006.01) |

(52) U.S. Cl.
CPC ............ *A61K 35/57* (2013.01); *A61K 35/741* (2013.01); *A61K 38/43* (2013.01); *A61P 29/00* (2018.01); *A61K 45/06* (2013.01); *A61P 35/00* (2018.01); *A61P 37/06* (2018.01)

(58) Field of Classification Search
CPC .................................................. A61K 35/37
See application file for complete search history.

(56) References Cited

U.S. PATENT DOCUMENTS

| | | | |
|---|---|---|---|
| 6,410,516 B1 | 6/2002 | Baltimore et al. | |
| 2010/0179103 A1* | 7/2010 | Desai | B82Y 5/00 514/58 |

OTHER PUBLICATIONS

English bibliographic information for Kim et al., KR 2015031922 A, Mar. 25, 2015. (Year: 2015).*
Vane et al., "Inflammation and the Mechanism of Action of Anti-Imflammatory Drugs", FASEB J, vol. 1, pp. 89-96; 1987.
Nakano et al., "Glucocorticoids Suppress Group II Phospholipase A2 Production by Blocking mRNA Synthesis and Post-transcriptional Expression*", The Journal of Biological Chemistry, vol. 265, No. 21, pp. 12745-12748; 1990.

(Continued)

*Primary Examiner* — Rosanne Kosson
(74) *Attorney, Agent, or Firm* — Hoffmann & Baron, LLP

(57) ABSTRACT

The present invention relates to the use of eggshell membrane compositions to activate levels of nuclear factor kappa-light-chain-enhancer of activated B cells ("NF-κB") in the gut of a host in need thereof and methods of treating conditions related to NF-κB dysregulation.

6 Claims, 5 Drawing Sheets

: *in vitro* NF-κB activity of fermentation and enzymatic hydrolyzates of eggshell membrane in human peripheral blood mononuclear cells.

FH = Fermentation Hydrolyzate, EH = Enzymatic Hydrolyzate, * = $p < 0.05$ versus Untreated Control

(56) References Cited

OTHER PUBLICATIONS

Kenneth K. Wu, M.D., Ph.D., "Aspirin and Other Cyclooxygenase Inhibitors: New Therapeutic Insights", Seminars in Vascular Medicine, vol. 3, No. 2, pp. 107-112; 2003.
Bingham III, M.D. et al., "Predictors of Response to Cyclo-Oxygenase-2 Inhibitors in Osteoarthritis: Pooled Results from Two Identical Trials Comparing Etoricoxib, Celecoxib, and Placebo", Pain Medicine, vol. 12, pp. 352-361; 2011.
Israel et al., "The Effect of Inhibition of 5-Lipoxygenase by Zileuton in Mild-to-Moderate Asthma", Annals of Internal Medicine, vol. 119, No. 11, pp. 1059-1066; 1993.
Knorr et al., "Montelukast, a Leukotriene Receptor Antagonist, for the Treatment of Persistent Asthma in Children Aged 2 to 5 Years", Pediatrics, vol. 108, No. 3, pp. 1-10; 2001.
Sen et al., "Multiple Nuclear Factors Interact with the Immunoglobulin Enhancer Sequences", Cell, vol. 46, pp. 705-716; 1986.
TD Gilmore, "Introduction to NF-κB: players, pathways, perspectives", Oncogene, vol. 25, pp. 6680-6684; 2006.
Akira et al., "Pathogen Recognition and Innate Immunity", Cell, vol. 124, pp. 783-801; 2006.
Hayden et al., "NF-κB and the Immune Response", Oncogene, vol. 25, pp. 6758-6780; 2006.
Beg et al., "Tumor Necrosis Factor and Interleukin-1 Lead to Phosphorylation and Loss of IκBα: a Mechanism for NF-κB Activation", Molecular and Cellular Biology, vol. 13, No. 6, pp. 3301-3310; 1993.
Flodström et al., "Cytokines Activate the Nuclear Factor κB (NF-κB) and Induce Nitric Oxide Production in Human Pancreatic Islets", FEBS Letters, vol. 385, pp. 4-6; 1996.
Schreck et al., "Nuclear Factor κB: An Oxidative Stress-Responsive Transcription Factor of Eukaryotic Cells (A Review)", Free Rad. Res. Comms., vol. 17, No. 4, pp. 221-237; 1992.
J. G. Scandalios, "Oxidative Stress: Molecular Perception and Transduction of Signals Triggering Antioxidant Gene Defenses", Brazilian Journal of Medical and Biological Research, vol. 38, pp. 995-1014; 2005.
Cooper et al., "Ultraviolet B Regulation of Transcription Factor Families: Roles of Nuclear Factor-kappa B (NF-κB) and Activator Protein-1 (AP-1) in UVB-Induced Skin Carcinogenesis", Current Cancer Drug Targets, vol. 7, pp. 325-334; 2007.
Reelfs et al., "Ultraviolet A Radiation-Induced Immediate Iron Release is a Key Modulator of the Activation of NF-κB in Human Skin Fibroblasts", J. Invest. Dermatol., vol. 122, pp. 1440-1447; 2004.
Kono et al., "NADPH Oxidase-Derived Free Radicals are Key Oxidants in Alcohol-Induced Liver Disease", J. Clin. Invest., vol. 106, pp. 867-872; 2000.
She et al., "Iron Activates NF-κB in Kupffer Cells", Am. J. Physical Gastrointest Liver Physiol., vol. 283, pp. G719-G726; 2002.
Yamamoto et al., "Role of the NF-κB Pathway in the Pathogenesis of Human Disease States", Current Molecular Medicine, vol. 1, pp. 287-296; 2001.
Prajapati et al., "Role of NFκB in Various Immunological & Inflammatory Disorders", International Journal of Toxicological and Pharmacological Research, vol. 2, No. 1, pp. 35-39; 2010.
Courtois et al., Mutations in the NF-κB Signaling Pathway: Implications for Human Disease, Oncogene, vol. 25, pp. 6831-6843; 2006.

Tak et al., "NF-κB: A Key Role in Inflammatory Diseases", The Journal of Clinical Investigation, vol. 107, No. 1, pp. 7-11; 2001.
Brand et al., "Activated Transcription Factor Nuclear Factor-Kappa B is Present in the Atherosclerotic Lesion", J. Clin. Invest., vol. 97, No. 7, pp. 1715-1722; 1996.
Hajra et al., "The NF-κB Signal Transduction Pathway in Aortic Endothelial Cells is Primed for Activation in Regions Predisposed to Atherosclerotic Lesion Formation", PNAS, vol. 97, No. 16, pp. 9052-9057; 2000.
Akama et al., "Amyloid β-peptide Stimulates Nitric Oxide Production in Astrocytes Through an NFκB-dependent Mechanism", Proc. Natl. Acad. Sci., vol. 95, pp. 5795-5800; 1998.
Akama et al., "β-Amyloid Stimulation of Inducible Nitric-Oxide Synthase in Astrocytes Is Interleukin-1β- and Tumor Necrosis Factor-α (TNFα)-dependent, and Involves a TNFα Receptor-associated Factor- and NFκB-inducing Kinase-dependent Signaling Mechanism*", The Journal of Biological Chemistry, vol. 275, No. 11, pp. 7918-7924; 2000.
Miterski et al., "Inhibitors in the NFκB Cascade Comprise Prime Candidate Genes Predisposing to Multiple Sclerosis, Especially in Selected Combinations", Genes and Immunity, vol. 3, pp. 211-219; 2002.
Yan et al., "NF-κB, a Potential Therapeutic Target for the Treatment of Multiple Sclerosis", CNS & Neurological Disorders—Drug Targets, vol. 7, pp. 536-557; 2008.
Patel et al., "Role of NF-κB in the Pathogenesis of Diabetes and its Associated Complications", Pharmacological Reports, vol. 61, pp. 595-603; 2009.
Andreasen et al., "Type 2 Diabetes is Associated with Altered NF-κB DNA Binding Activity, JNK Phosphorylation, and AMPK Phosphorylation in Skeletal Muscle after LPS", PloS One, vol. 6, No. 9, pp. 1-8; 2011.
Bassères et al., "Nuclear Factor-κB and Inhibitor of κB Kinase Pathways in Oncogenic Initiation and Progression", Oncogene, vol. 25, pp. 6817-6830; 2006.
Kordes et al., "Transcription Factor NF-κB is Constitutively Activated in Acute Lymphoblastic Leukemia Cells", Leukemia, vol. 14, pp. 399-402; 2000.
Bauerle et al., "Inhibition of Nuclear Factor-kappa B Differentially Affects Thyroid Cancer Cell Growth, Apoptosis, and Invasion", Molecular Cancer, vol. 9, No. 117, pp. 1-13; 2010.
Bowie et al., "Vitamin C Inhibits NF-κB Activation by TNF Via the Activation of p38 Mitogen-Activated Protein Kinase", J. Immunol, vol. 165, pp. 7180-7188; 2000.
Simmonds et al., "NF-κB and its Relevance to Arthritis and Inflammation", Rheumatology, vol. 47, pp. 584-590; 2008.
Brown et al., "The Roles of the Classical and Alternative Nuclear Factor-κB Pathways: Potential Implications for Autoimmunity and Rheumatoid Arthritis", Arthritis Research & Therapy, vol. 10, No. 212, pp. 1-14; 2008.
Han et al., "Ap-1 and NF-κB Regularion in Rheumatoid Arthritis and Murine Collagen-Induced Arthritis", Autoimmunity, vol. 28, pp. 197-208; 1998.
Seetharaman et al., "Essential Role of T Cell NF-κB Activation in Collagen-Induced Arthritis", The American Association of Immunologists, The Journal of Immunology, vol. 163, pp. 1577-1583; 1999.
Shi et al., "Hydrolysate from Eggshell Membrane Ameliorates Intestinal Inflammation in Mice", Int. J. Mol. Sci, 15, 22728-22742 (2014).

* cited by examiner

Figure 1: *in vitro* NF-κB activity of fermentation and enzymatic hydrolyzates of eggshell membrane in human peripheral blood mononuclear cells.

FH = Fermentation Hydrolyzate, EH = Enzymatic Hydrolyzate, * = $p < 0.05$ versus Untreated Control

Figure 2: *in vitro* NF-κB activity of fermentation, enzymatic, & chemical hydrolyzates of eggshell membrane in the human THP-1 monocyte cell line.

FH = Fermentation Hydrolyzate, EH = Enzymatic Hydrolyzate, CH = Chemical Hydrolyzate,
* = $p < 0.05$ versus Untreated Control Figure 3: Caliper measurements of ankle swelling from Day 9 through Day 17 in collagen-induced arthritis in naïve control, arthritis control, methotrexate-treated, & NEM-treated rats.

\* = $p < 0.05$ versus Arthritis Control

METHODS FOR TREATING NUCLEAR FACTOR KAPPA-LIGHT-CHAIN-ENHANCER OF ACTIVATED B CELL (NF-KB) DYSREGULATION IN A HOST IN NEED THEREOF USING EGGSHELL MEMBRANE COMPOSITIONS

CROSS-REFERENCE TO RELATED APPLICATIONS

This application is a divisional of, and claims priority to, U.S. application Ser. No. 15/528,335 filed May 19, 2017 which is a National Stage application of International Application No. PCT/US2015/054742, filed Oct. 8, 2015, which is incorporated by reference herein in its entirety.

FIELD OF THE INVENTION

The present invention relates to the use of eggshell membrane compositions to activate levels of nuclear factor kappa-light-chain-enhancer of activated B cells ("NF-κB") in the gut of a host in need thereof and methods of treating conditions related to NF-κB dysregulation.

BACKGROUND OF THE INVENTION

Inflammation plays a critical role in defending a host from infectious invaders and repairing tissues following injury. However, when inflammation does not resolve appropriately it can have significant detrimental effects within the body. It is well-accepted that chronic inflammation contributes to the pathogenesis of countless diseases. This type of inflammation commonly leads to tissue destruction and/or organ failure and can lead to symptoms that can have a drastic impact on the quality of life of those afflicted.

When tissue injury occurs through physical, chemical or biological means, phospholipids in the cell membranes are first metabolized to arachidonic acid, which is further metabolized to prostaglandins through the well-known cyclooxygenase enzymes (COX-1 & COX-2). The resulting prostaglandins primarily produce the well-recognized outward effects seen at the site of injury, including edema (swelling), erythema (redness), localized fever, and pain. Simultaneously, pro-inflammatory cytokines, particularly Interleukin 1 beta (IL-1β) and Tumor Necrosis Factor alpha (TNF-α), are released by local cells and also by immune cells when they arrive at the site of injury. These pro-inflammatory cytokines amplify both the inflammatory process and the pain cascade through feedback mechanisms as demonstrated in FIG. 4.

Treatments for chronic inflammatory conditions can target any of a number of enzymes or receptors within this cascade. For example, corticosteroids suppress phospholipase $A_2$ activity, slowing the release of arachidonic acid from the conversion of phospholipids within the cell membrane, and aspirin (acetylsalicylic acid), one of the most widely known Non-Steroidal Anti-Inflammatory Drugs (NSAIDs), non-selectively and irreversibly inhibits cyclooxygenase-1 (COX-1), one of the primary enzymes in the production of downstream prostaglandins. Few, if any, treatments however have specifically targeted the role that NF-κB plays in this inflammatory cascade.

NF-κB is a protein complex family found in the cytoplasm of nearly all animal cell types and the DNA binding activities of this transcription factor family were first reported in 1986. Once activated and translocated to the nucleus, NF-κB controls the transcription of multiple genes involved in rapidly responding to negative or harmful external cellular stimuli as demonstrated in FIG. 5.

Active NF-κB is a heterodimeric protein which consists of either a p50 monomer with a RelA monomer (p50/RelA) or a p52 monomer with a RelB monomer (p52/RelB). The Rel proteins (RelA & RelB) are a highly conserved (from species to species) DNA-binding domain known as the Rel Homology Domain (RHD) which also contain transcription activation domains (TADs) that enable them to activate target gene expression. The monomers p50 & p52 are known as NF-κB proteins and consist mainly of ankyrin repeats with two N-terminal serine residues. They also contain the RHD domain, however they lack the TADs found in the Rel proteins and therefore cannot activate gene expression in either their monomeric form or in a homodimeric (p50/p50 or p52/p52) form. They must be coupled with a Rel protein to activate the DNA sequences known collectively as KB sites.

Prior to activation, the p50/RelA heterodimer exists in the cytoplasm as an inactive complex in which it is bound to an inhibitor of KB known as IκBα, and the p52/RelB heterodimer exists as an inactive p100/RelB heterodimer in the cytoplasm. There are two well-accepted paths to activation of NF-κB, the canonical or classical pathway and the non-canonical or alternative pathway. In the canonical pathway, IκBα is serially phosphorylated by an inhibitor of κB kinase (IKK-α), targeting IκBα for ubiquitination and eventual destruction in the proteasome. In the non-canonical pathway, p100 which functions as an inhibitor of κB (IκB), is serially phosphorylated by an inhibitor of κB kinase (IKK-β) and is partially degraded to the active p52 protein. These IκB kinases (IKK-α & IKK-β) exist in a trimeric form in the cytoplasm in what is known as the IKK complex. The IKKs are coupled with the regulatory scaffold protein NF-κB Essential Modulator (NEMO) to prevent continuous activation of NF-κB. In either pathway (canonical or non-canonical), the IKK complex is activated when signaling molecules bind to cell surface receptors. Bacterial or viral antigens, various cytokines (e.g. IL-1β, TNF-α, etc.), oxidative stress, ultraviolet irradiation, and free radicals are just some of the stimuli known to trigger activation of one or the other of the NF-κB pathways, either through directly binding to these cell surface receptors or by causing other signaling molecules to be formed which then bind to the receptors.

NF-κB was initially investigated for its critical role in regulating the immune response to infection. However, in the decades since its discovery, the dysregulation of NF-κB has been associated with numerous classical inflammatory diseases such as sepsis, asthma, rheumatoid arthritis (RA), and inflammatory bowel disease (IBD). Interestingly, a number of diseases that are not obviously inflammatory in nature have also been associated with NF-κB dysregulation, including atherosclerosis, Alzheimer's disease, multiple sclerosis, diabetes, and various cancers.

In general, the NF-κB dysregulation involved in disease pathology is that of over-activation, inappropriate activation, or chronic activation. In a classic inflammatory disease like asthma, airway irritants that are only mildly irritating to a normal airway cause severe inflammation in an asthmatic airway (i.e. over-activation). In inflammatory bowel diseases such as Crohn's or gluten intolerance, components of a person's diet that are not irritating to a normal gut, cause acute inflammation which can lead to severe intestinal damage (i.e. inappropriate activation). Or, in the case of rheumatoid arthritis, the body of an RA sufferer becomes sensitized to fragments of degraded cartilage (i.e. glycosaminoglycans, type II collagen, etc.) leading to an autoimmune reaction to one's own cartilage ultimately leading to further and severe cartilage degradation (i.e. chronic activation). Logically, to treat these diseases one would seek to de-activate or inhibit NF-κB in some manner to restore its proper regulation.

Applicants have surprisingly discovered that activation of NF-κB in the gut of a host has a positive effect on many diseases and conditions, as well as treating NF-κB dysregulation. Without being bound by theory, Applicants believe that activation of NF-κB in the gut of a host results in a decrease or deactivation of NF-κB systemically in the host.

SUMMARY OF THE INVENTION

The herein invention provides a method for activating NF-κB in the gut of a host in need thereof. The method comprises orally administering an effective amount of a composition consisting essentially of eggshell membrane, and/or eggshell membrane isolates and/or eggshell membrane hydrolyzates to the host.

The herein invention also provides a method for systemically decreasing NF-κB in a host in need thereof. The method comprises orally administering an effective amount of a composition consisting essentially of eggshell membrane, and/or eggshell membrane isolates and/or eggshell membrane hydrolyzates to the host.

In one embodiment, the host in need thereof suffers from a pulmonary disease or condition. The pulmonary disease or condition is selected from the group consisting of asthma, chronic obstructive pulmonary disease, bronchitis, emphysema, cystic fibrosis, pulmonary edema, sarcoidosis, acute respiratory distress syndrome, pneumoconiosis, pulmonary hypertension, hypersensitivity pneumonitis, and allergies.

The pulmonary disease or condition is also selected from the group consisting of mild, periodic lung congestion; mild, periodic coughing; mild, periodic sinus congestion; periodic sneezing; or mild, periodic lung inflammation.

In another embodiment, the host in need thereof suffers from a disease or condition affecting the brain or nervous system. The disease or condition affecting the brain or nervous system is selected from the group consisting of Alzheimer's disease, fibromyalgia, temporary ischemic attack, vasculitis, cerebral edema, multiple sclerosis, Huntington's disease, amyotrophic lateral sclerosis, Parkinson's disease, epilepsy, and neurodegeneration.

The disease or condition affecting the brain or nervous system is also selected from the group consisting of periodic forgetfulness; mild, periodic nerve tingling or phantom sensations; or mild, periodic muscle twitches.

In yet another embodiment, the host in need thereof suffers from a cardiovascular disease or condition. The cardiovascular disease or condition is selected from the group consisting of atherosclerosis, cardiomyopathy, Marfan Syndrome, pericarditis, heart valve disease, rheumatic heart disease, peripheral artery disease, venous thrombosis, inflammatory heart disease, hypertension, hyperlipidemia, and hypertriglyceridemia.

The cardiovascular disease or condition is also selected from the group consisting of mild vascular inflammation; mildly elevated blood pressure; mildly elevated cholesterol; or mildly elevated triglycerides.

In the method of the invention, the host in need thereof is also a host suffering from a disease or condition of the gastrointestinal system. The disease or condition of the gastrointestinal system is selected from the group consisting of Crohn's disease, ulcerative colitis, gastritis, diverticulitis, irritable bowel syndrome, celiac disease, gastroesophageal reflux disease, dyspepsia, peptic ulcer, and duodenal ulcer.

The disease or condition of the gastrointestinal system is also selected from the group consisting of mild, periodic diarrhea; mild, periodic constipation; mild, periodic stomach cramping or pain; mild stomach inflammation; mild intestinal inflammation; or mild colon inflammation.

According to an embodiment of the invention, the host in need thereof suffers from cancer. The cancer is selected from the group consisting of leukemia, lymphoma, breast cancer, bladder cancer, colon cancer, prostate cancer, pancreatic cancer, ovarian cancer, and thyroid cancer.

In another embodiment, the host in need thereof suffers from a disease selected from the group consisting of non-alcoholic steatohepatitis, hepatitis, nephritis, dermatitis, conjunctivitis, and gingivitis.

The invention provides for a host in need thereof suffering from a condition in which NF-κB dysregulation is present.

According to an embodiment of the invention, the method further comprises co-administering an anti-inflammatory agent to said host.

The anti-inflammatory agent is selected from the group consisting of an inhaled corticosteroid; an oral corticosteroid; a non-steroidal anti-inflammatory drug; an omega-3 or omega-6 polyunsaturated fatty acid; *Boswellia* species or *Boswellia* extract; turmeric or turmeric extract; curcumin or cucuminoids; white willow bark or white willow bark extract; proteolytic enzymes; collagen or collagen hydrolyzates; pine bark extract; a vitamin or vitamin pre-cursor; and a mineral.

DETAILED DESCRIPTION OF THE INVENTION

Figure 1:
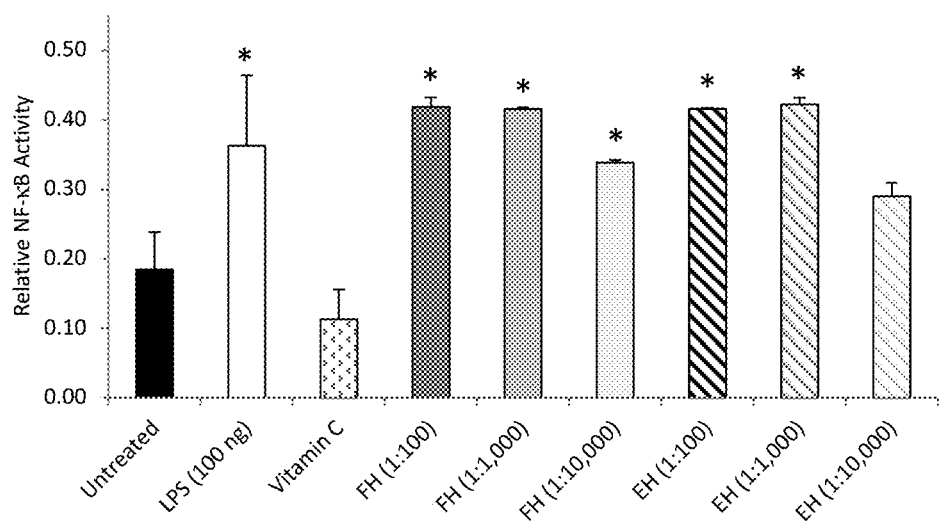
FIG. 1: This figure exemplifies in vitro NF-κB activity of fermentation and enzymatic hydrolyzates of eggshell membrane in human peripheral blood mononuclear cells.

The present invention relates to methods for activating NF-κB in the gut of a host in need thereof. The present invention also relates to methods for systemically deactivating NF-κB in a host in need thereof. The methods comprise orally administering an effective amount of a composition consisting essentially of eggshell membrane, and/or eggshell membrane isolates and/or eggshell membrane hydrolyzates to the host.

By "activating," it is meant that endogenous NF-κB that is present in the cells of the host is activated, i.e. called into action by the immune response provoked in the gut of the host in response to the eggshell membrane composition. As a result of said activation, levels of active NF-κB in the gut of the host are increased.

By "systemically deactivating" it is meant that the amount of active NF-κB is decreased in the body of the host in need thereof. The "body" encompasses all parts of the host's physical body. Body includes extremities, organ systems, brain, skin, and skeletal system of the host.

By "the gut," it is meant to include the alimentary canal in its entirety. For example, gut includes all parts of the gut of the host from the pylorus to the anus. Gut is also meant to include the foregut, midgut and hindgut of the host. This includes, for example, the stomach, the large intestine and the small intestine. In a preferred embodiment, the activation of NF-κB occurs in the small and large intestine.

By "a host in need thereof," is meant any host that can benefit from systemic deactivation of NF-κB. The host is any mammal, amphibian, reptile, fish or bird. Mammals include, for example, humans, domestic animals and farm animals. Domestic animals include, for example, cats and dogs. Farm animals include, for example, cows, horses, pigs, chickens and sheep. Amphibians include any amphibian including, for example, frogs, toads, salamanders and newts. Reptiles include any reptile including, for example, snakes, lizards and turtles. Fish include any fish including salt and fresh water fish. Birds include any bird.

The deactivation of NF-κB occurs in any part of the host's body. For example, the deactivation of NF-κB occurs in the lungs, brain, heart, or gut. In a preferred embodiment, the deactivation of NF-κB occurs systemically in the host.

Examples of "a host in need thereof" includes a host that suffers from a pulmonary disease or condition, a disease or condition affecting the brain or nervous system, a cardiovascular disease or condition, a disease or condition of the gastrointestinal system, cancer, other diseases and conditions or a condition in which NF-κB dysregulation is present.

The pulmonary disease or condition can be any pulmonary disease or condition. For example, the pulmonary disease or condition is selected from the group consisting of asthma, chronic obstructive pulmonary disease, bronchitis, emphysema, cystic fibrosis, pulmonary edema, sarcoidosis, acute respiratory distress syndrome, pneumoconiosis, pulmonary hypertension, hypersensitivity pneumonitis, and allergies. Furthermore, the pulmonary disease or condition is also selected from the group consisting of mild, periodic lung congestion; mild, periodic coughing; mild, periodic sinus congestion; periodic sneezing; or mild, periodic lung inflammation.

The disease or condition affecting the brain or nervous system can be any disease or condition that affects the brain or nervous system. For example, the disease or condition affecting the brain or nervous system is selected from the group consisting of Alzheimer's disease, fibromyalgia, temporary ischemic attack, vasculitis, cerebral edema, multiple sclerosis, Huntington's disease, amyotrophic lateral sclerosis, Parkinson's disease, epilepsy, and neurodegeneration.

The disease or condition affecting the brain or nervous system is also selected from the group consisting of periodic forgetfulness; mild, periodic nerve tingling or phantom sensations; or mild, periodic muscle twitches.

The cardiovascular disease or condition can be any disease or condition affecting the cardiovascular system. For example, the cardiovascular disease or condition is selected from the group consisting of atherosclerosis, cardiomyopathy, Marfan Syndrome, pericarditis, heart valve disease, rheumatic heart disease, peripheral artery disease, venous thrombosis, inflammatory heart disease, hypertension, hyperlipidemia, and hypertriglyceridemia. The cardiovascular disease or condition is also selected from the group consisting of mild vascular inflammation; mildly elevated blood pressure; mildly elevated cholesterol; or mildly elevated triglycerides.

The disease or condition of the gastrointestinal system can be any disease or condition affecting the gastrointestinal system of the host. For example, the disease or condition of the gastrointestinal system is selected from the group consisting of Crohn's disease, ulcerative colitis, gastritis, diverticulitis, irritable bowel syndrome, celiac disease, gastroesophageal reflux disease, dyspepsia, peptic ulcer, and duodenal ulcer. The disease or condition of the gastrointestinal system is also selected from the group consisting of mild, periodic diarrhea; mild, periodic constipation; mild, periodic stomach cramping or pain; mild stomach inflammation; mild intestinal inflammation; or mild colon inflammation.

Cancer can be any form of cancer. For example, the cancer is selected from the group consisting of leukemia, lymphoma, breast cancer, bladder cancer, colon cancer, prostate cancer, pancreatic cancer, ovarian cancer, and thyroid cancer.

Other diseases include any disease that could benefit from activation of NF-κB in the gut. For example, other diseases are selected from the group consisting of non-alcoholic steatohepatitis, hepatitis, nephritis, dermatitis, conjunctivitis, and gingivitis.

Diseases and conditions in which NF-κB dysregulation is present include any disease or condition in which one of the contributing factors is NF-κB dysregulation. For example, this includes a disease or condition in which NF-κB dysregulation plays a role in the etiology and/or pathology of the disease, and refers to a disease state in which NF-κB is abnormally activated (either over-activated, inappropriately activated, or chronically activated) at a cellular level, either locally or systemically, and which contributes to the development and/or progression of the disease state either directly, or indirectly by affecting other systems of the body.

In addition, abnormally activated NF-κB refers to a host having cellular levels of non-inhibited or active NF-κB that are elevated compared to a respective normal host of the same species within the same cell type having the same gender, weight, height, and/or age as the treated host. This effect commonly occurs through NF-κB's subsequent activation of the host's immune system leading to an abnormal chronic inflammatory response. In the case of asthma, this inflammation occurs in the lungs. In the case of Alzheimer's disease this inflammation occurs in the brain tissue. In the case of arthritis, this inflammation occurs in tissues of the joint (e.g. tendons, ligaments, the synovium, articular cartilage, etc.). In the case of cardiovascular disease, this inflammation occurs in the heart tissue or blood vessel walls. In the case of diabetes, this inflammation occurs in the pancreas. In the case of inflammatory bowel disease (IBD), this inflammation occurs in varying locations within the intestinal tract depending upon the specific type of IBD (e.g. Crohn's disease, Irritable Bowel Syndrome (IBS), ulcerative colitis, etc.). In the case of multiple sclerosis, this inflammation occurs in nerve and muscle tissues.

In another aspect of the invention, the host in need thereof is in a "pre-diseased" state. For example, in a pre-diseased state NF-κB dysregulation may be occurring at the earliest of stages, but there are no or insufficient clinical symptoms of disease which could afford a diagnosis of such disease, and the subject would otherwise be considered 'healthy'. Although the subject is considered 'healthy' they would benefit from the administration of a composition that is the subject of this invention and such treatment could even possibly prevent the subject from reaching a diseased state. Thus, in one embodiment, the host in need thereof is a 'healthy' host.

Administration

According to the invention, the composition consisting essentially of eggshell membrane, and/or eggshell membrane isolates and/or eggshell membrane hydrolyzates is orally administered to the host in need thereof. Oral administration includes administration via mouth in any suitable form. For example, suitable forms include pills, tablets, capsules, powders, gummies, troches, and elixirs. The composition is also orally administered as an ingredient in foods, dietary supplements, or pharmaceuticals.

One of ordinary skill in the art can envision other oral delivery formats and these are intended to be encompassed within the scope of the present invention.

Effective Amount

By "effective amount" is meant any amount that effectively activates NF-κB in the gut of the host in need thereof. This amount is determined taking body weight of the host into consideration. In a preferred embodiment, the daily dose of the composition consisting essentially of eggshell membrane, and/or eggshell membrane isolates and/or eggshell membrane hydrolyzates is approximately 500 mg per day for a human of average size (e.g. 132 lbs. or 60 kg). For smaller hosts such as canines or felines, the daily dose of the composition is 15 mg/kg (6.8 mg/lb.). For larger hosts such as a horse, the daily dose of the composition is 5 mg/kg (2.3 mg/lb.).

The daily dose is administered at once or in 2 or more smaller doses that add up to the approximate daily dose for the host. For example, an approximately 500 mg/day dose can be taken as approximately 250 mg in the morning and 250 mg in the evening. Sustained release formulations are also contemplated.

Compositions of the Invention

The compositions of the invention consist essentially of eggshell membrane, and/or eggshell membrane isolates and/or eggshell membrane hydrolyzates. The composition also includes combinations of processed eggshell membrane, eggshell membrane isolates and hydrolyzates.

The eggshell membrane material is obtained by methods that preferably include the step of separating the eggshell membrane from the egg yolk, egg white, and eggshell prior to subsequent processing and isolation steps. The eggshell membrane, processed eggshell membrane, and eggshell membrane isolates and hydrolyzates are preferably free of any embryo components or traces thereof, e.g., animal tissue, blood or body fluid components, which are detrimental or undesirable for the contemplated use of the products or product combinations.

Typically, the source of eggshell membrane will be from cracked chicken eggs, where the eggshell membrane is still attached to the eggshell. The eggshell membrane can be separated from the eggshell in any convenient manner. Preferably, the eggshell membrane is separated from the eggshell in the absence of any unwanted substance that would remain in the source material. Unwanted substances will primarily include calcium carbonate from residual eggshell. However, small amounts of this calcium source may be beneficial in certain applications, e.g., dietary supplements.

Methods for separating eggshell membrane from the eggshell can include a purely mechanical manner as, for instance, by rolling and pulling the membranes away from the washed shells after removal of the yoke and albumen of fresh or uncooked eggs. Mechanical methods of separating eggshell membranes from cooked eggs are also contemplated.

A combination of mechanical and chemical means of separating the eggshell membrane from the eggshell can also be used, such as agitating coarsely chopped eggshells containing the adhering membranes in the presence of a dilute acid until the membrane separates from the shell and separating the released membranes from the shells. U.S. Pat. No. 3,194,732 to Neuhauser provides a more detailed discussion of methods for separating eggshell membrane from eggshells, which is incorporated herein by reference.

The method also preferably includes drying the separated eggshell membrane to produce eggshell membrane flakes of various dimensions and subsequently grinding or milling the eggshell membrane flakes to produce an eggshell membrane powder with a particle size between 50-500 microns. Powdering is accomplished using standard grinding, milling, or pulverizing procedures to treat eggshell membrane flakes containing about 10% moisture or less. Sizing is conducted using a series of screens.

In a preferred embodiment, the powdered eggshell membrane is subjected to chemical or enzymatic hydrolysis. The resulting slurry typically contains a soluble fraction containing predominantly proteins or smaller peptides and other water-soluble fractions and an insoluble fraction containing predominantly high-molecular weight proteins and other insoluble fractions.

The chemical hydrolysis of eggshell membrane can be accomplished using mineral acids, organic acids, mineral bases, organic bases, metal catalysts, amino acids, reducing agents, oxidizing agents, or any other chemical that catalyzes hydrolysis or solubilize the material in some way. Enzymatic hydrolysis of eggshell membrane can be accomplished using enzymes from plant or animal sources or from microorganisms such as bacteria or yeasts. Types of enzymes that can be used in the hydrolysis are: proteases, collagenases, elastases, hydrolases, lyases, ligases, or any other enzymes that catalyze hydrolysis or solubilize the material in some way.

In another embodiment, powdered eggshell membrane is subjected to fermentation with a live inoculum. The inoculum is comprised of living microorganisms such as bacteria, yeasts, fungi, or combinations thereof. Some example microorganism species are: *Bacillus subtilis, Bacillus licheniformis, Bacillus stearothermophilus, Streptomyces griseus, Serratia marcescens, Rhizopus niveus, Rhizopus oryzae, Penicillium duponti, Aspergillus oryzae, Aspergillus niger, Aspergillus melleus, Aspergillus sojae, Aspergillus saitoi, Candida albicans, Saccharomyces cerevisiae, Saccharomyces fragilis*, etc. The resulting slurry typically contains a soluble fraction containing predominantly proteins or smaller peptides and other water-soluble fractions and an insoluble fraction containing predominantly high-molecular weight proteins and other insoluble fractions. It is preferred that the eggshell membrane isolates and hydrolyzates are prepared without substantially altering the natural material found in the eggshell membrane.

Preferably, the materials found in the eggshell membrane are naturally occurring, i.e. not substantially altered as a result of the processes used to prepare the isolates or hydrolyzates.

By the terminology "natural material," "naturally occurring material," or "naturally occurring active material," derived from eggshell membrane it is intended that the material derived from eggshell membrane contains a significant amount of at least one ingredient or component of the eggshell membrane that is substantially unaltered from the untreated or unprocessed eggshell membrane, in terms of its function as an ingredient useful for therapeutic applications. By substantially unaltered is meant that the selected or desired ingredient(s) or component(s) substantially retain(s) its/their physical characteristics and is/are not significantly decomposed, digested or cleaved. However, other components or ingredients may be altered in certain isolates or hydrolyzates. For example, hydrolyzates prepared by enzymatic treatment may result in naturally occurring proteins being at least partially digested. Preferably, the majority of the naturally occurring ingredients found in the eggshell membrane are substantially unaltered and, more preferably, substantially all of the naturally occurring ingredients are substantially unaltered. Although the physical characteristics of individual components of the eggshell membrane remain substantially unaltered, the overall composition or amounts of different components can be altered depending on the desired composition for a particular isolate or hydrolyzate.

The compositions can include mechanically processed eggshell membrane, such as flakes or powder, or eggshell membrane isolates or hydrolyzates. The eggshell membrane isolates or hydrolyzates can be in liquid, semi-solid or solid form, e.g. a partially dehydrated powdered form containing varying amounts of liquid or moisture.

Although the present invention is directed to chicken eggshell membrane (i.e. *Gallus gallus* or *Gallus domesticus*), one of ordinary skill in the art could envision the use of any other fowl eggshell membrane such as duck, goose, ostrich, pigeon, quail, etc. Furthermore, in some examples the present application has been described with reference to a method for eggshell membrane enzyme hydrolysis and subsequent extraction and purification of naturally occurring eggshell membrane substances. One skilled in the art can easily ascertain various methods for eggshell membrane hydrolysis. Such equivalents are intended to be encompassed within the scope of the present invention.

The invention also contemplates therapeutic compositions which include eggshell membrane in combination with a therapeutically acceptable carrier or vehicle. A therapeutically acceptable carrier is intended to be any material that does not interfere with the therapeutic effect(s) of the invention, but which can serve to deliver the therapeutic composition orally. This can include typical pharmaceutical excipients and/or binders such as calcium carbonate, microcrystalline cellulose, silica, starch, mannitol, fructose, sucrose, sorbitol, citric acid, alginate, calcium phosphate, gelatin, glycerin, pectin, hypromellose, magnesium stearate, polyethyleneglycol, methyl paraben, etc.

A composition that contains both (a) eggshell membrane, and/or eggshell membrane isolates and/or eggshell membrane hydrolyzates and (b) an anti-inflammatory agent is also contemplated by the invention.

By "anti-inflammatory agent" it is meant to include any compound that is known to provide an anti-inflammatory affect in a host. For example, the anti-inflammatory agent is selected from the group consisting of an inhaled corticosteroid; an oral corticosteroid; a non-steroidal anti-inflammatory drug; an omega-3 or omega-6 polyunsaturated fatty acid; *Boswellia* species or *Boswellia* extract; turmeric or turmeric extract; curcumin or cucuminoids; white willow bark or white willow bark extract; proteolytic enzymes; collagen or collagen hydrolyzates; pine bark extract; a vitamin or vitamin pre-cursor; and a mineral.

A composition that contains both (a) eggshell membrane, and/or eggshell membrane isolates and/or eggshell membrane hydrolyzates; and (b) a probiotic, prebiotic and/or a combination thereof is also contemplated by the invention. A composition that contains both (a) eggshell membrane, and/or eggshell membrane isolates and/or eggshell membrane hydrolyzates; and (b) digestive enzymes, L-glutamine, or fiber is also contemplated by the invention. Such compositions are useful for improving gut health or in the treatment of diseases or conditions including those of the gut.

A composition that contains both: (a) eggshell membrane, and/or eggshell membrane isolates and/or eggshell membrane hydrolyzates; and (b) cinnamon, or chromium picolinate, or *Gymnema sylvestre*, or alpha lipoic acid, or white kidney bean extract is also contemplated by the invention. Such compositions are useful in blood glucose control.

A composition that contains both: (a) eggshell membrane, and/or eggshell membrane isolates and/or eggshell membrane hydrolyzates; and (b) niacin, or omega-3 or omega-6 polyunsaturated fatty acids, or coenzyme Q10 or, tocotrienol is also contemplated. Such compositions are useful in the treatment of diseases or conditions including cardiovascular diseases or conditions or for improving cardiovascular health.

A composition that contains both: (a) eggshell membrane, and/or eggshell membrane isolates and/or eggshell membrane hydrolyzates; and (b) *Ginko biloba*, or vitamin D are also contemplated. Such compositions are useful for improving brain health, and treating diseases or conditions of the brain and nervous system.

A composition that contains both: (a) eggshell membrane, and/or eggshell membrane isolates and/or eggshell membrane hydrolyzates; and (b) antioxidants including for example quercitin, pine bark extract, and green tea extract are also contemplated. Such compositions are useful for treating for cancer, and/or the symptoms associated with cancer, and/or providing immune support.

EXAMPLES

The following non-limiting examples have been carried out to illustrate various embodiments of the invention:

Example 1: Preparation of Eggshell Membrane Flakes and Powder

The following example is illustrative of the preparation of eggshell membrane flakes and powder. Chicken eggshells with attached eggshell membranes were obtained from an egg breaking facility. The eggshell membrane was first separated from eggshells. Eggshell membrane flakes were collected and immediately dried to a moisture content of less than 10%. Powdering of the dried eggshell membrane flakes was accomplished using standard milling or pulverizing procedures. The powder was subsequently sized by screening the pulverized powder through a series of calibrated screens to produce a particle size range from 50-500 microns.

Example 2: Preparation of Eggshell Membrane Hydrolyzate Via Fermentation

The following example is illustrative of the preparation of an eggshell membrane hydrolyzate utilizing a fermentation process. Eggshell membrane powder prepared as in Example 1 was placed into a water solution containing an inoculum comprised of bacteria and yeasts. This slurry was allowed to ferment for about 24 hours at room temperature (~25° C.). The slurry was filtered to remove any particles of un-digested eggshell membrane powder. The fermentation hydrolyzate (filtered liquid) was stored refrigerated or frozen when not being used immediately and is referred to as ESM-FH.

Example 3: Preparation of Eggshell Membrane Hydrolyzate Via Enzymatic Hydrolysis The following example is illustrative of the preparation of an eggshell membrane hydrolyzate utilizing an enzymatic digestion. Eggshell membrane powder prepared as in Example 1 was placed into a buffered solution (pH~9) containing purified alkaline protease from *Bacillus licheniformis* in a 1:10 ratio to membrane powder (w/w). This slurry was allowed to stir for up to 5 days at ~55° C. The slurry was allowed to cool and was filtered to remove any particles of un-digested eggshell membrane powder. The enzymatic hydrolyzate (filtered liquid) was stored refrigerated or frozen when not being used immediately and is referred to as ESM-EH.

Example 4: Preparation of Eggshell Membrane Hydrolyzate Via Chemical Hydrolysis

The following example is illustrative of the preparation of an eggshell membrane hydrolyzate utilizing chemical hydrolysis. Eggshell membrane powder prepared as in Example 1 was placed into an alkaline solution (pH~14) containing 3M sodium hydroxide. This slurry was allowed to stir for about 8 hours at ~55° C. The slurry was allowed to cool and was filtered to remove any particles of un-digested eggshell membrane powder. The filtered liquid was neutralized (pH~7) with 12M hydrochloric acid with cooling to absorb excess heat of neutralization. The chemical hydrolyzate was stored refrigerated or frozen when not being used immediately and is referred to as ESM-CH.

Example 5: Preparation of NEM® (ESM Technologies, Carthage, Mo.) Brand Eggshell Membrane Product The following example is illustrative of the preparation of an eggshell membrane product that is a combination of eggshell membrane, as prepared in Example 1, and a hydrolyzate of eggshell membrane, as prepared in Examples 2-4. Eggshell membrane powder prepared as in Example 1 was placed into a jacketed ribbon blender. While blending, eggshell membrane hydrolyzate is carefully sprayed onto the eggshell membrane powder. The blender jacket is warmed to at least 185° F. and a slight vacuum is pulled on the vessel to facilitate the removal of moisture. Once the moisture level reaches less than 10% by weight, the dried powder is removed from the blender and passed through a grinder to grind up any lumps that may have formed. This product (NEM®) was stored under ambient conditions in a double poly-lined cardboard box.

Example 6: Determination of In Vitro NF-κB Activity of Eggshell Membrane Hydrolyzates in Human Peripheral Blood Mononuclear Cells The following example is illustrative of the determination of the in vitro NF-κB activity of eggshell membrane hydrolyzates in human Peripheral Blood Mononuclear Cells (PBMCs). PBMCs were isolated from healthy volunteers and cultured at $3.2 \times 10^6$ cells/well in culture medium [RPMI-1640 medium supplemented with 10% fetal bovine serum (FBS), L-glutamine (2 mM), penicillin (100 U/mL) and streptomycin (100 mg/mL)]. Cells were plated in duplicate. Eggshell membrane hydrolyzates, as prepared in Examples 2 and 3, were diluted 1:1 with phosphate buffered saline (PBS) filtered through a 0.22 micron cellulose acetate disc to sterilize them (e.g. remove bacteria, yeasts, and/or molds). The hydrolyzates were then diluted (1:100; 1:1,000; 1:10, 000) with culture medium. Each dilution (60 μL) was added to a culture well and the cells were incubated at 37° C., 5% $CO_2$ for 4 hours. A known activator of NF-Kb, lipopolysaccharide (LPS)(100 ng/mL), was used as a positive control and a known inhibitor of NF-κB, Vitamin C (ascorbic acid)(20 mM) (Bowie & O'Neill, 2000), was used as a comparator of the inhibitory effect in LPS-treated cells. Activity was also compared to un-treated cells. Cells were pelletized by centrifuging at 150×g (1200 rpm) for 3 minutes and the supernatant was discarded. Cell lysates were prepared from the incubated cultures via bead milling. The whole-cell lysates were assayed for NF-κB activity via a commercially available Enzyme-linked Immunosorbent assay (ELISA) kit (TransAM® NF-κB p65 ELISA Assay kit; Active Motif—Carlsbad, Calif.). Samples were assayed in duplicate and were corrected for total protein content via the Bradford method (Bio-Rad Laboratories—Hercules, Calif.). The relative activity of NF-κB in PBMCs for each solution evaluated (untreated, LPS, Vitamin C, ESM-FH, & ESM-EH) can be seen in FIG. 1.

Figure 2:
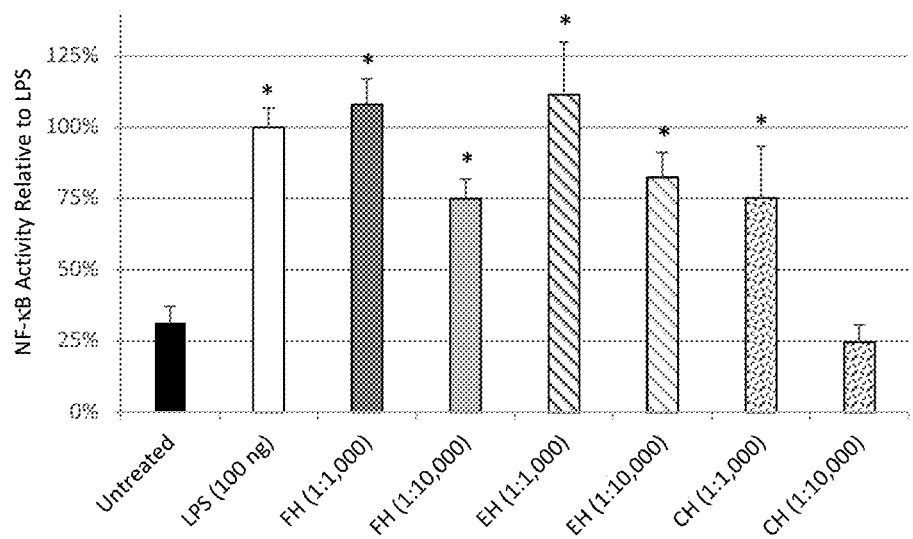
FIG. 2: This figure exemplifies in vitro NF-κB activity of fermentation, enzymatic, & chemical hydrolyzates of eggshell membrane in the human THP-1 monocyte cell line.

Example 7: Determination of In Vitro NF-κB Activity of Eggshell Membrane Hydrolyzates in a Human Monocyte Cell Line The following example is illustrative of the determination of the in vitro NF-κB activity of eggshell membrane hydrolyzates in a human monocyte cell line (THP-1). THP-1 cells were obtained from American Type Culture Collection (Manassas, Va.) and cultured at $2.0 \times 10^5$ cells/well in culture medium [RPMI-1640 medium supplemented with 10% fetal bovine serum (FBS), 2-mercaptoethanol (0.05 mM), and 1% penicillin-streptomycin]. Cells were plated using a volume of 350 μL per well in duplicate with n=3 individual plates. Eggshell membrane hydrolyzates, as prepared in Examples 2, 3, & 4 were filtered through a 0.2 micron polyethersulfone disc to sterilize them (e.g. remove bacteria, yeasts, and/or molds). The hydrolyzates were then diluted (1:1,000; 1:10, 000) with culture medium. Each dilution was added to a culture well and the cells were incubated at 37° C., 5% $CO_2$ for 4 hours. A known activator of NF-Kb, lipopolysaccharide (LPS)(100 ng/mL), was used as a positive control and un-treated cells were used as a negative control. Cells were pelletized by centrifuging at 150×g (1200 rpm) for 3 minutes and the supernatant was discarded. Cell lysates were prepared from the incubated cultures by adding 45 μL of complete lysis buffer (containing lysis buffer, protease inhibitor cocktail, and dithiothreitol). The whole-cell lysates were assayed for NF-κB activity via a commercially available Enzyme-linked Immunosorbent assay (ELISA) kit (TransAM® NF-κB p65 ELISA Assay kit; Active Motif—Carlsbad, Calif.). Samples were assayed in duplicate and were corrected for total protein content via the Bradford method (Bio-Rad Laboratories—Hercules, Calif.). The relative activity of NF-κB in THP-1 cells for each solution evaluated (untreated, LPS, ESM-FH, ESM-EH, & ESM-CH) can be seen in FIG. 2.

Figure 3:
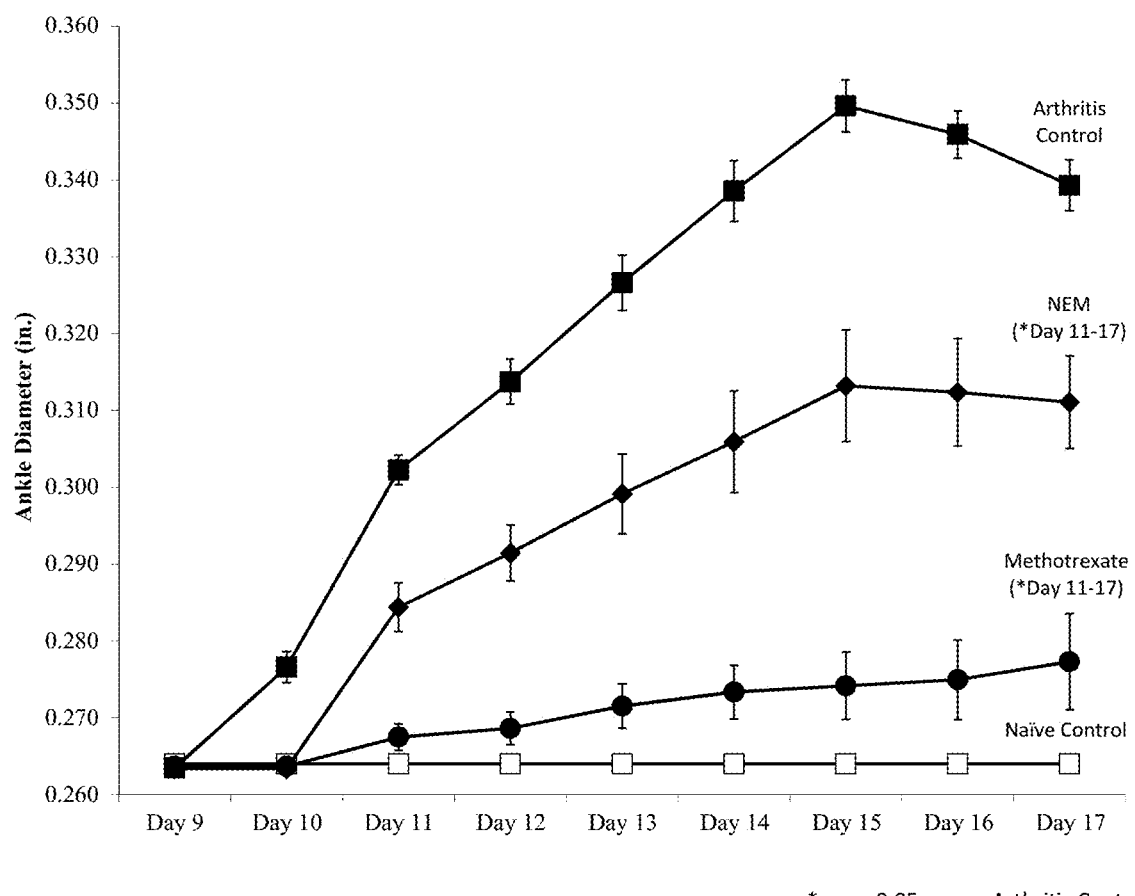
FIG. 3: This figure exemplifies caliper measurements of ankle swelling from Day 9 through Day 17 in collagen-induced arthritis in naïve control, arthritis control, methotrexate-treated, & NEM-treated rats.
Figure 4:
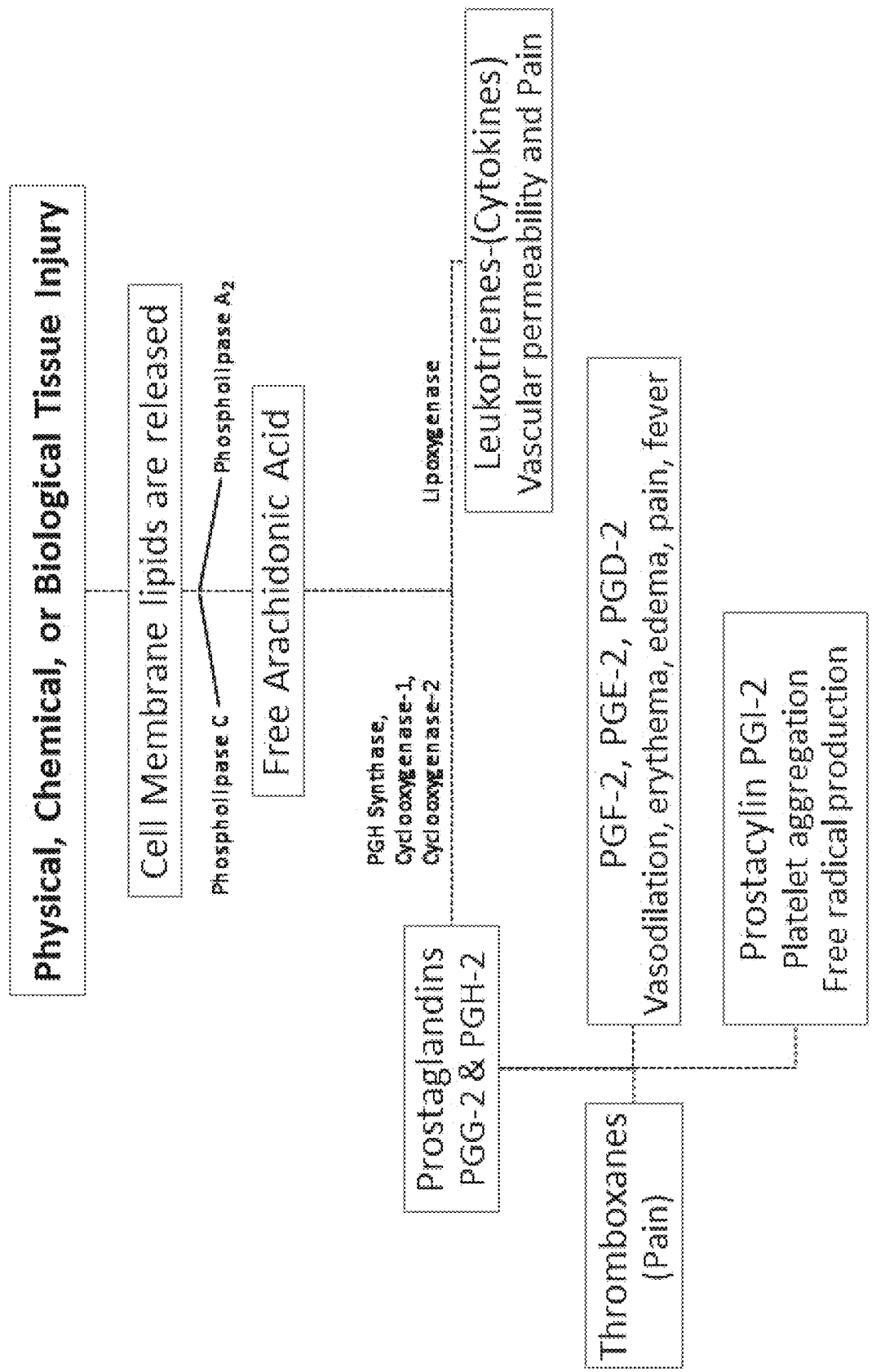
FIG. 4: This figure depicts the inflammation cascade resulting from physical, chemical, or biological tissue injury.
Figure 5:
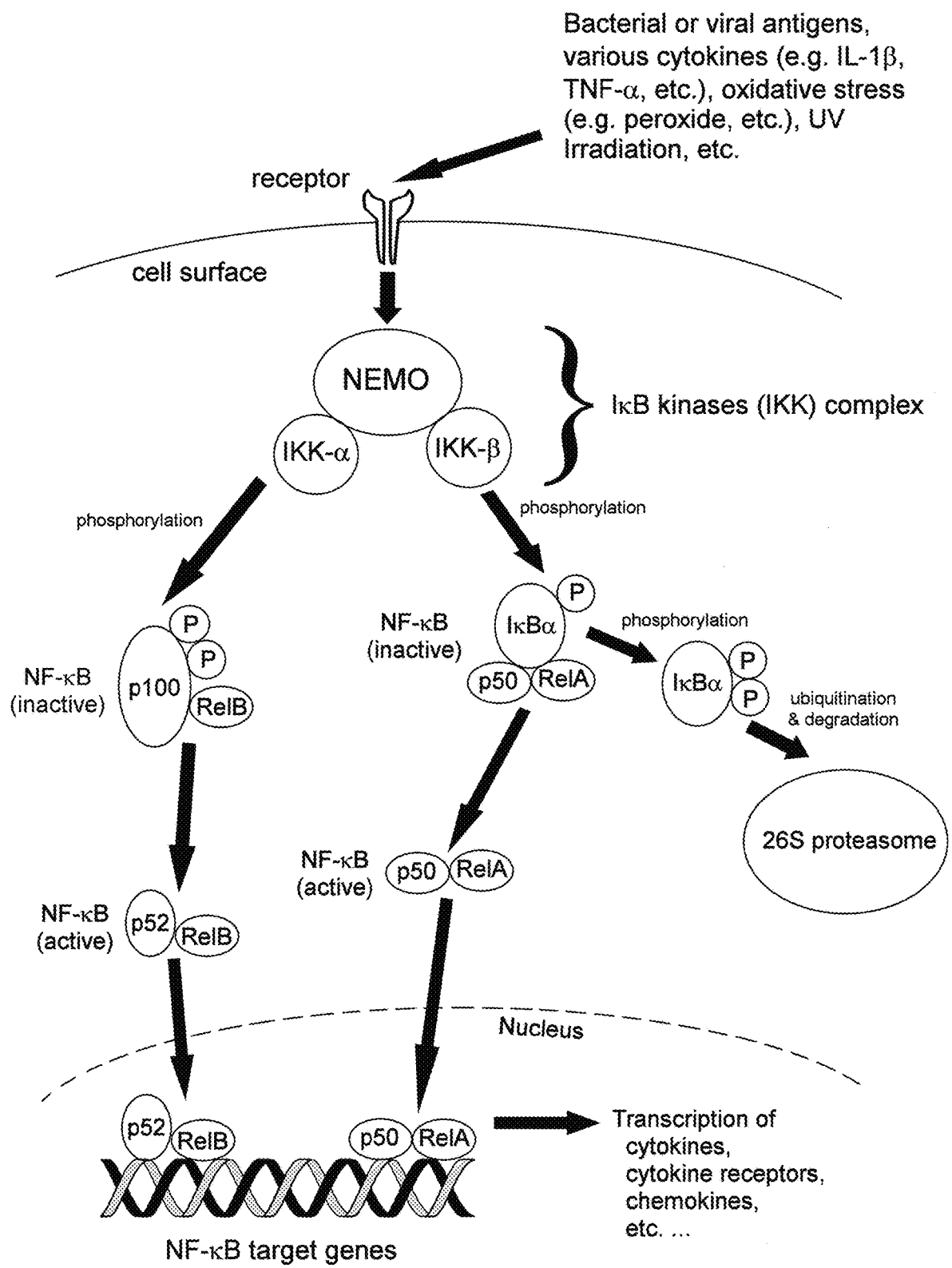
FIG. 5: This figure exemplifies activation of the NF-kB signaling pathway.

Example 8: Efficacy of Orally Administered NEM® Brand Eggshell Membrane in an NF-κB-Mediated Animal Model of Rheumatoid Arthritis The following example is illustrative of the determination of the in vivo efficacy of an orally administered eggshell membrane product (trade name NEM®) in an NF-κB-mediated animal model of rheumatoid arthritis. NF-κB is known to be activated in human rheumatoid arthritis (Simmonds & Foxwell, 2008; Brown, Claudio, & Siebenlist, 2008) and is well-established to play a key role in the collagen-induced arthritis animal model of rheumatoid arthritis (Han, Boyle, Manning, & Firestein, 1998; Seetharaman, Mora, Nabozny, Boothby, & Chen, 1999). Female Lewis rats (10 per group, randomized by body weight) (Charles River Laboratories, Inc.—Wilmington, Mass.) weighing 115-139 grams were given either NEM® (52 mg/kg body weight) or vehicle (0.5% methylcellulose in water) by oral gavage for 14 days. An additional group received methotrexate (0.0075 mg/kg body weight)(Sigma-Aldrich—St. Louis, Mo.) as a comparator, beginning at Day 0 (no pre-feed). Following the pre-feed (on Day 0), rats were anesthetized with Isoflurane and injected with 400 µl of Difco™ Freund's Incomplete Adjuvant (Detroit, Mich.) containing 2 mg/ml porcine type II collagen (Chondrex—Portland, Oreg.) at 2 sites at the base of the tail (200 µl per injection site). Seven days later, rats received a booster injection of 100 µl at a single site at the base of the tail. The vehicle only group was previously divided into a naïve control (no arthritis) and an arthritis control (no treatment). Animals were housed 3-4 to a cage under standard laboratory conditions (67-76° F., 30-70% humidity, 12-hour light/dark cycles) with access to food and water ad libitum. On study days 9-17, caliper measurements of ankle swelling were made with a Digitrix II Point Micrometer (Fowler—Newton, Mass.). The results of caliper measurements of ankle swelling from Day 9 through Day 17 in collagen-induced arthritis in naïve control, arthritis control, methotrexate-treated, & NEM-treated rats can be seen in FIG. 3.

Example 9: Efficacy of Orally Administered NEM® Brand Eggshell Membrane in a Human Suffering from Inflammatory Bowel Disease The following example is illustrative of the efficacy of an orally administered eggshell membrane product (trade name NEM®) in treating a human suffering from a form of inflammatory bowel disease. A human male suffered from frequent severe bouts of diarrhea accompanied by bloating and painful cramping. These episodes would often last 3-4 days, requiring numerous trips to the restroom each day. There would be periods of 1-2 days without these severe symptoms, followed by another multi-day episode of severe diarrhea, bloating, and cramping. The subject was subsequently formally diagnosed with ulcerative colitis via a biopsy taken from a colonoscopy. The subject was unable to treat the condition with prescribed medication due to side effects. An exclusion diet, in which fatty foods, fried foods, and other foods high in either carbohydrates or fiber are avoided or kept to a minimum, helped to reduce the severity of the diarrheal episodes but did little to reduce the frequency. The subject began taking one capsule containing 500 mg of NEM® as prepared in Example 5 before each meal, daily. After about 7-10 days, the severity and frequency of diarrheal episodes began to lessen. After about 2 months of the NEM® regimen the subject would experience only 1 or 2 diarrheal episodes per week, each lasting 1 or 2 days. Following the addition of digestive enzymes to address stomach cramping and *Lactobacillus acidophilus* probiotics and L-glutamine to support intestinal healing to the regimen, the subject was able to incorporate more of the foods avoided in the exclusion diet, particularly meats and breads. Following this regimen, the subject would generally only experience one episode of diarrhea requiring only a single trip to the restroom. After about 6 months of this regimen, the subject was able to gradually reduce the dosing to a single maintenance dose of one NEM® capsule, digestive enzymes, L-glutamine, and probiotics, with only an occasional episode of diarrhea. A 2-year follow-up colonoscopy confirmed that the severe inflammation in the colon had subsided and the subject no longer suffered from ulcerative colitis.

Example 10: Efficacy of Orally Administered NEM® Brand Eggshell Membrane in a Human Suffering from Cardiovascular Disease The following examples are illustrative of the efficacy of an orally administered eggshell membrane product (trade name NEM®) in treating a human suffering from cardiovascular disease. A human male with a long history of cardiovascular disease (hyperlipidemia, hypertriglyceridemia, hypertension, atherosclerosis, etc.) had an initial untreated lipid panel of: Total cholesterol (TC)=186 mg/dL, low density lipoprotein (LDL)=108 mg/dL, high density lipoprotein (HDL)=42 mg/dL, and triglycerides (TG)=181 mg/dL. The subject was unable to treat the condition with prescribed lipid lowering medication due to side effects and diet and exercise had failed to adequately control the disease. The subject was treating his hypertension with 100 mg/day of atenolol. This resulted in a resting systolic/diastolic blood pressure (bp) of 146/84 mm Hg. The subject had also had four cardiac stents placed to treat atherosclerotic stenosis (narrowing) of various cardiac blood vessels. The subject consumed one 500 mg capsule per day of NEM® as prepared in Example 5 for about 12 months before noticing an effect on lipid panel results. The subject continued the NEM® regimen for an additional approximately 12 months (about 2 years total). Follow-up lipid panel results were: TC=138 mg/dL, LDL=80 mg/dL, HDL=41 mg/dL, and TG=84 mg/dL. All lipid results were now within normal ranges. The subject also found it necessary to reduce the atenolol dose from 100 mg/day to 25 mg/day. Even with this reduction in medication the subject now had a resting bp of 102/78 mm Hg.

A second human male with a recent history of cardiovascular disease (hyperlipidemia & hypertriglyceridemia only) was being treated with 10 mg/day of atorvastatin. Treated lipid panel results for this subject were: TC=207 mg/dL, LDL=114 mg/dL, HDL=47 mg/dL, and TG=247 mg/dL. This subject had an untreated resting bp within normal range. The subject consumed one 500 mg capsule per day of NEM® as prepared in Example 5 for about 2 years. Follow-up lipid panel results were: TC=150 mg/dL, LDL=81 mg/dL, HDL=46 mg/dL, and TG=113 mg/dL. All lipid results were now within normal ranges.

Example 11: Efficacy of Orally Administered NEM® Brand Eggshell Membrane in a Human Suffering from a Form of Liver Disease The following example is illustrative of the efficacy of an orally administered eggshell membrane product (trade name NEM®) in treating a human suffering from a form of liver disease. A human male was found to have mildly elevated liver enzymes through routine health screening. Initial liver enzyme panel results were: alanine transaminase (ALT)=81 and aspartate transaminase (AST)=41. Due to the subject's obesity and lack of other concurrent findings, the subject was diagnose with non-alcoholic steatohepatitis, a form of liver disease. The primary treatment for this condition is weight loss. The subject consumed one 500 mg capsule per day of NEM® as prepared in Example 5 for about 2 years. Follow-up liver enzyme panel results were: ALT=40 and AST=21. Liver enzymes were now within normal ranges.

Example 12: Efficacy of Orally Administered NEM® Brand Eggshell Membrane in a Human Having Joint Stiffness and Discomfort The following example is illustrative of the efficacy of an orally administered eggshell membrane product (trade name NEM®) in treating a non-diseased human having joint stiffness and discomfort. A human male suffered from joint discomfort in both shoulders and both hips, as well as joint stiffness and discomfort in both knees. The subject had not been diagnosed with arthritis and the discomfort did not appear to worsen significantly over many years as would be the case with degenerative joint disease like arthritis. The subject would experience aching in his shoulders and hips while lying in bed which would disturb his sleep. This pattern of sleep disturbance would generally occur 1-2 times per week. The subject also had difficulty in getting to a kneeling or seated position on the floor and had great difficulty in returning to a standing position. The subject consumed three 500 mg capsules per day of NEM® as prepared in Example 5 for about 4 weeks. The subject was no longer awakened from his sleep by any discomfort in his shoulders or hips. The subject's knees were also much less stiff with very little discomfort and the subject was now better able to get to a kneeling or seated position on the floor and had much less difficulty in returning to a standing position.

Example 13: Efficacy of Orally Administered NEM® Brand Eggshell Membrane in a Human Suffering from Fibromyalgia The following example is illustrative of the efficacy of an orally administered eggshell membrane product (trade name NEM®) in treating a human suffering from fibromyalgia. A human female with a 4-year history of fibromyalgia suffered from joint and connective tissue pain in numerous locations throughout the body and had extreme fatigue and was being treated with meloxicam (7.5 mg/day in the morning), ibuprofen (200 mg twice per day—morning & noontime), tramadol (50 mg/day before bedtime), and amitriptyline (20 mg/day before bedtime). The subject had been consuming NEM®, 500 mg/day prior to the diagnosis of fibromyalgia. The subject particularly experienced worsening symptoms from daily activities involving standing or walking for long periods (e.g. cleaning, laundry, shopping, etc.). Over time, the fibromyalgia really began to limit the subject's ability to perform daily activities. Even with the reduced activity level, the subject found the need to increase the tramadol to 50 mg twice per day (bid) and sometimes even 50 mg three times per day (tid) to control the painful symptoms. Due to concerns with the increasing need for the opioid analgesic tramadol (similar to a narcotic) and gastric burning from ibuprofen, the subject began to consume an additional 500 mg capsule per day (i.e. 500 mg twice per day) of NEM® as prepared in Example 5 about 4-5 hours apart for 3 weeks. The subject found significant relief from the pain and aching and was able to reduce the tramadol dosing to the original 50 mg/day and eliminate the ibuprofen completely.

What is claimed is:

1. A method for activating nuclear factor kappa-light-chain-enhancer of activated b cell (NF-KB) in the gut of a host in need thereof, the method comprising administering an effective amount of a composition consisting essentially of naturally occurring eggshell membrane, and/or eggshell membrane isolates and/or eggshell membrane hydrolyzates, or a combination thereof, to said host, wherein the host in need thereof suffers from a disease or condition of the gastrointestinal system, and wherein the method further comprises administering an anti-inflammatory agent to said host.

2. The method according to claim 1, wherein the anti-inflammatory agent is curcumin or curcuminoids.

3. The method according to claim 1, further comprising administering a therapeutically effective amount of an agent known for improving gut health or known for treating diseases or conditions of the gut to said host.

4. The method according to claim 3, wherein the gut-improving agent is selected from the group consisting of a probiotic, a prebiotic, digestive enzymes, L-glutamine, or fiber or a combination thereof.

5. The method according to claim 1, wherein the host is a human.

6. The method according to claim 1, wherein the host in need thereof suffers from a condition in which NF-KB dysregulation is present.

* * * * *